United States Patent [19]

Paparizos et al.

[11] Patent Number: 4,704,496

[45] Date of Patent: Nov. 3, 1987

[54] PROCESS FOR CONVERTING LIGHT HYDROCARBONS TO MORE READILY TRANSPORTABLE MATERIALS

[75] Inventors: Christos Paparizos, Willowick; Yihhong Song, Solon, both of Ohio

[73] Assignee: The Standard Oil Company, Cleveland, Ohio

[21] Appl. No.: 843,056

[22] Filed: Mar. 24, 1986

[51] Int. Cl.$^4$ .............................................. C07C 2/00
[52] U.S. Cl. .................................. 585/500; 585/415; 585/541; 585/648; 585/652; 585/654; 585/656; 585/700; 585/943; 585/650
[58] Field of Search ............... 585/500, 943, 700, 648, 585/541, 650, 652, 415, 654, 656

[56] References Cited

U.S. PATENT DOCUMENTS

| | | | |
|---|---|---|---|
| 1,907,274 | 5/1933 | Wheeler | 565/943 |
| 2,180,672 | 5/1936 | Frey | 196/10 |
| 2,221,658 | 11/1940 | Waterman et al. | 260/673 |
| 3,452,114 | 6/1969 | Friz et al. | 260/679 |
| 4,172,810 | 10/1979 | Mitchell et al. | 252/465 |
| 4,205,194 | 5/1980 | Mitchell et al. | 585/407 |
| 4,239,658 | 12/1980 | Mitchell et al. | 252/465 |
| 4,433,192 | 2/1984 | Olah | 298/486 |
| 4,443,644 | 4/1984 | Jones et al. | 585/500 |
| 4,443,645 | 4/1984 | Jones et al. | 585/500 |
| 4,443,646 | 4/1984 | Jones et al. | 585/500 |
| 4,443,647 | 4/1984 | Jones et al. | 585/500 |
| 4,443,648 | 4/1984 | Jones et al. | 585/500 |
| 4,443,649 | 4/1984 | Jones et al. | 585/500 |
| 4,450,310 | 5/1984 | Fox et al. | 585/400 |
| 4,465,893 | 8/1984 | Olah | 585/943 |
| 4,497,970 | 2/1985 | Young | 585/417 |
| 4,513,164 | 4/1985 | Olah | 585/700 |
| 4,544,785 | 10/1985 | Withers et al. | 585/500 |
| 4,547,610 | 10/1985 | Sofranko et al. | 585/500 |

OTHER PUBLICATIONS

G. E. Keller & M. M. Bhasin, Journal of Catalysis, 73, 9–19 (1982).

Primary Examiner—William R. Dixon, Jr.
Assistant Examiner—Cynthia A. Prezlack
Attorney, Agent, or Firm—Larry W. Evans; David J. Untener; Raymond F. Keller

[57] ABSTRACT

The invention relates to a process for converting light hydrocarbon feedstocks such as methane, ethane and/or natural gas, to higher molecular weight hydrocarbon products that are more readily handleable and transportable. The process comprises heating a gaseous mixture comprising said light hydrocarbon feedstocks and at least one oxide initiator selected from the group consisting of nitrogen oxides, sulfur trioxide and mixtures thereof at a temperature of at least about 600° C. for a period of time effective to provide said higher molecular weight hydrocarbon product. In one embodiment, the invention provides for a process for converting the feedstocks, to unsaturated compounds such as ethylene. The invention also relates to the higher molecular weight products obtained by the process of the invention.

32 Claims, No Drawings

PROCESS FOR CONVERTING LIGHT HYDROCARBONS TO MORE READILY TRANSPORTABLE MATERIALS

TECHNICAL FIELD

This invention relates to a process for converting light hydrocarbons to higher molecular weight and/or unsaturated hydrocarbon products. This invention further relates to the use of oxide initiators to promote such conversions where the yield of liquid products is enhanced.

BACKGROUND OF THE INVENTION

A major source of methane is natural gas which typically contains about 40-95% methane depending on the particular source. Other constituents include about 10% of ethane with the balance being made up of $CO_2$ and smaller amounts of propane, the butanes, the pentanes, nitrogen, etc.

Primary sources for natural gas are the porous reservoirs generally associated with crude oil reserves. From these sources come most of the natural gas used for heating purposes. Quantities of natural gas are also known to be present in coal deposits and are by-products of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing an occur at the wellhead or at a central processing station. Processed natural gas typically comprises a major amount of methane, and minor amounts of ethane, propane, the butanes, the pentanes, carbon dioxide and nitrogen. Generally, processed natural gas comprises from about 70% to more than about 95% by volume of methane. Natural gas is used principally as a source of heat in residential, commercial and industrial service.

Most processed natural gas is distributed through extensive pipeline distribution networks. As natural gas reserves in close proximity to gas usage decrease, new sources that are more distant require additional transportation. Many of these distant sources are not, however, amendable to transport by pipeline. For example, sources that are located in areas requiring economically unfeasible pipeline networks or in areas requiring transport across large bodies of water are not amendable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about $-162°$ C., transporting the gas, and revaporizing it are complex and energy intensive.

Still another approach has been the conversion of natural gas to higher molecular weight hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing. Known dehydrogenation and polymerization processes are available for the further conversion of ethane and ethylene to liquid hydrocarbons. In these ways, easily transportable commodities may be derived directly from natural gas at the wellhead. A drawback in implementing such processes has been in obtaining a sufficient conversion rate of natural gas to higher molecular weight hydrocarbons.

The conversion of methane to higher molecular weight hydrocarbons at high temperatures, in excess of about 1200° C. is known. These processes are, however, energy intensive and have not been developed to the point where high yields are obtained even with the use of catalysts. Some catalysts that are useful in these processes (e.g., chlorine) are corrosive under such operating conditions.

Low temperature pyrolysis (e.g., to 250° C. and 500° C.) of hydrocarbon feedstocks to higher molecular weight hydrocarbons is described in U.S. Pat. Nos. 4,433,192; 4,497,970; and 4,513,164. The processes described in these patents utilize heterogeneous systems and solid acid catalysts. In addition to the solid acid catalysts, the reaction mixtures described in the and U.S. Pat. Nos. 4,497,970 and 4,513,16 include oxidizing agents. Among the oxidizing agents disclosed are air, $O_2$-$O_3$ mixtures, S, Se, $SO_3$, $N_2O$, NO, $NO_3$, F, etc.

The catalytic oxidative coupling of methane at atmospheric pressure and temperatures of from about 500° C. to 1000° C. has been investigated by G. E. Keller and M. M. Bhasin. These researchers reported the synthesis of ethylene via oxidative coupling of methane over a wide variety of metal oxides supported on an alpha alumina structure in *Journal of Catalysis*, 73, 9-19 (1982). This article discloses the use of single component oxide catalysts that exhibited methane conversion to higher order hydrocarbons at rates no greater than 4%. The process by which keller and Bhasin oxidized methane was cyclic, varying the feed composition between methane, nitrogen and air (oxygen) to obtain higher selectivities.

Methods for converting methane to higher molecular weight hydrocarbons at temperatures in the range of about 500° C. to about 1000° C. are disclosed in U.S. Pat. Nos. 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about 4% overall conversion. In addition to synthesizing hydrocarbons, the processes disclosed in these references also produce a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,172,810; 4,205,194; and 4,239,658 disclose the production of hydrocarbons including ethylene, benzene, ethane, propane and the like, in the presence of a catalyst-reagent composition which comprises: (1) a group VIII noble metal having an atomic number of 45 or greater, nickel, or a group Ib noble metal having an atomic number of 47 or greater; (2) a group VIb metal oxide which is capable of being reduced to a lower oxide; and (3) a group IIa metal selected from the group consisting of magnesium and strontium composited with a passivated, spinel-coated refractory support or calcium composited with a passivated, non-zinc containing spinel-coated refractory support. The feed streams used in the processes disclosed in these patents do not contain oxygen. Oxygen is avoided for the purposes of avoiding the formation of coke in the catalyst. Oxygen is generated for the reaction from the catalyst; thus periodic regenerations of the catalysts are required.

U.S. Pat. No. 4,450,310 discloses a methane conversion process for the production of olefins and hydrogen comprising contacting methane in the absence of oxygen and in the absence of water at a reaction temperature of at least 500° C. with a catalyst comprising the mixed oxides of a first metal selected from lithium, sodium, potassium, rubidium, cesium and mixtures thereof, and optionally a promoter metal selected from copper, rhenium, tungsten, zirconium, rhodium, and mixtures thereof.

It would be advantageous to provide a process for converting light hydrocarbons such as methane, ethane, natural gas, and the like to higher molecular weight hydrocarbons that are more readily handleable and transportable. It would be advantageous if this process were suitable for thermally cracking ethane and enhancing the liquid product yield thereof.

SUMMARY OF THE INVENTION

A process is described for converting light hydrocarbon feedstocks such as methane, ethane and/or natural gas, to higher molecular weight hydrocarbon products that are more readily handleable and transportable. The process comprises heating a gaseous mixture comprising said light hydrocarbon feedstocks and at least one oxide initiator selected from the group consisting of nitrogen oxides, sulfur trioxide and mixtures thereof at a temperature of at least about 600° C. for a period of time effective to provide said higher molecular weight hydrocarbon product. In one embodiment, the invention provides for a process for converting the feedstocks to unsaturated compounds such as ethylene. The invention also relates to the higher molecular weight products obtained by the process of the invention.

DESCRIPTION OF THE PREFERRED EMBODIMENTS

The light hydrocarbon feedstocks that are converted to higher molecular weight hydrocarbons in accordance with the process of the invention are typically hydrocarbons containing from 1 to about 4 carbon atoms. These hydrocarbons include, for example, methane, ethane, ethylene, propane, propylene, the butanes, the butylenes, ethylene, acetylene, and the like, as well as mixtures of two or more of said hydrocarbons.

In a particularly advantageous embodiment of the invention, the light hydrocarbon feedstocks are methane, ethane, and/or natural gas. The natural gas that can be used can be either wellhead natural gas, as discussed above, or processed natural gas. The composition of processed natural gas varies with the needs of the ultimate user. A typical processed natural gas composition contains about 70% by weight methane, about 10% by weight ethane, 10 to 15% of $CO_2$ and the balance being made up of smaller amounts of propane, butane and nitrogen.

The conversion of the light hydrocarbon feedstocks to higher molecular weight hydrocarbon products and/or unsaturated hydrocarbon products is conducted in the presence of at least one oxide initiator which is selected from the group consisting of nitrogen oxides, sulfur trioxides, or mixtures of these. Among the nitrogen oxides which are useful as initiators include $N_2O$, $NO$, $N_2O_3$, $N_2O_4$, $N_2O_5$, and mixtures of such nitrogen oxides. $N_2O$ is a preferred nitrogen oxide initiator.

The amount of oxide initiator mixed with the hydrocarbon feedstock can be varied from about 0.1 to about 30% by volume based on the volume of the feedstock. More often the amount of initiator will be in the range of 0.1 to 10%, and most often in the range of 1-5%. It has been discovered that the oxide initiators which are utilized in the present invention are reactive enough to assist in initiating the desired reaction leading to the formation of higher molecular weight hydrocarbons, and in particular, liquid hydrocarbons, but the oxides are not so active as to cause undesirable oxidation reactions that would convert the hydrocarbons prematurely to carbon monoxide and carbon dioxide.

One advantage of the process of the present invention is that the oxide initiators can be premixed with the hydrocarbon feedstock, and this mixture then can be heated up to the pyrolysis temperature without undesirable side reactions. Alternatively the feedstock gases can be heated to an elevated temperature, and the oxide initiator added to the heated feedstock. The former procedure is preferred. Another advantage of the use of the oxide initiators of the present invention is that the oxides not only enhance the feedstock conversion to the desired higher molecular weight hydrocarbons, but also suppress the formation of undesirable carbon residues.

The conversion of light hydrocarbon feedstocks to higher molecular weight hydrocarbon products and/or unsaturated hydrocarbon products can be conducted at temperatures above about 600° C., and the temperatures may be as high as 1500° C. Preferably, the pyrolysis reaction is conducted at temperatures above about 850° C., and even more preferably between about 1000° C. to about 1250° C.

The pyrolysis reaction can be conducted at subatmospheric, atmospheric or at elevated pressures up to about 50 atmospheres. Generally, the reaction is conducted at a pressure of from about 1 to about 10 atmospheres, and more generally at about 1 or 2 atmosphere pressure.

The period of time for heating the gaseous mixture of light hydrocarbon materials and oxide initiator (or residence time in the reactor) is generally a time which is sufficient to provide the desired conversion to higher molecular weight hydrocarbon products and/or unsaturated products. However, the reaction time or residence time should not be so long as to provide sufficient time for the products obtained to decompose. Accordingly, contact or residence time in the range of from about 0.1 to about 3000 milliseconds have been found to be useful with contact times in the range of from about 1 to about 1000 milliseconds being preferred. Contact times of from about 5 to about 800 milliseconds are most preferred with many light hydrocarbon feedstocks.

The composition of the higher molecular weight hydrocarbon products produced in accordance with the process of the invention may be somewhat dependent upon the nature of the light hydrocarbons that are initially used as feedstock, and the condition under which they are processed. For example, if the light hydrocarbon that is initially used is methane or natural gas, the higher molecular weight hydrocarbon product will typically consist of hydrocarbons containing two or more carbon atoms. These hydrocarbon products generally consist of mixtures of both aliphatic and aromatic materials. Since the process of the present invention is well-suited to a continuous, cyclic process, the lighter weight gaseous hydrocarbon products such as ethane or propane, etc. can be separated from the more desirable higher molecular weight hydrocarbon products (generally liquid) and recycled in the process for further conversion to even higher molecular weight hydrocarbon products. Unsaturation hydrocarbons present in the hydrocarbon products obtained in this invention include ethylene and acetylene which may be recovered as products of the process or recycled through the process for conversion to higher molecular weight products.

The preferred higher molecular weight hydrocarbon products made by the process of the present invention are aliphatic and/or aromatic products that are sufficiently liquid to be readily handleable and transportable in conventional pipeline systems. Included in this preferred group are hydrocarbons containing at least about 5 carbon atoms, more particularly, aromatic compounds containing at least 6 carbon atoms. The references in this application to "liquid hydrocarbons" is intended to include hydrocarbons that are substantially in the liquid form at a temperature of about 25° C. and a pressure of one atmosphere.

The apparatus that can be used in the process of the present invention can be any conventional pyrolysis reactor system that is adapted to the specific gaseous reactants and high molecular weight products provided for in the process of the invention. Such pyrolysis reactors include fired tubular heaters, pebble-bed heaters and regenerative furnaces, but fired tubular heaters are the generally preferred type of reactor. These reactors can be made from a variety of materials which can withstand high temperatures. A more detailed description of such apparatus can be found in the Encyclopedia of Chemical Technology, Kirk and Othmer, Ed. Third Edition, Vol. 9, pp. 400-11 which is incorporated herein by reference. The design and construction of such apparatus is within the skill of the art and thus need not be described further herein.

In one preferred embodiment, the process of the invention is carried out in the absence of any solid catalyst, particularly solid acid catalysts or oxidizers.

In order to further illustrate the present invention, the following examples are provided. Unless otherwise indicated in the following examples and elsewhere in the specification and claims, all parts and percentages of the products are by weight, and those of the feeds are by volume; all temperatures are in degrees centigrade.

EXAMPLES 1-3

In each of the following Examples 1-3, the feedstock indicated in the table including the $N_2O$, is introduced into a quartz tube reactor (0.5 cm. in diameter) that is surrounded by an electric furnace to provide the desired temperature. The control sample contains no oxide initiator. In operation, the gaseous feed composition is advanced through the quartz tube and the product is collected in containers cooled with dry ice and acetone. The "liquids" identified in the following table are those materials which condensed in the cooled containers excluding the water formed. The weight percentage of the liquid hydrocarbon products is calculated by weighing the liquids formed and dividing that weight by the amount of hydrocarbon in the feed composition and multiplying by 100. The selectivity is defined by dividing the weight of product formed by the weight of consumed hydrocarbon feed and multiplying by 100. The conversion is defined by dividing the hydrocarbon that is converted by the hydrocarbon consumed and multiplying by 100. The gases that are obtained from the process are analyzed using a Carl 400GC chromatograph. The temperature employed in the following Examples 1-3 and the control is 1125° C., and the residence time in the examples is about 100 milliseconds.

TABLE

| Example<br>Feed (v) | Control<br>100% $CH_4$ | 1<br>98% $CH_4$<br>2% $N_2O$ | 2<br>99% $CH_4$<br>1% $N_2O$ | 3<br>95% $CH_4$<br>5% $N_2O$ |
|---|---|---|---|---|
| 1 Product Analysis (% w) | | | | |
| Methane Conversion | 3.8 | 16.4 | 11.1 | 18.5 |
| Selectivity to Liquids | 40.4 | 42.3 | 43.8 | 57.8 |
| Selectivity to Ethylene | 32.5 | 17.5 | 20.8 | 17.5 |
| Selectivity to Acetylene | 18.7 | 15.1 | 15.2 | 15.0 |
| Liquids formed (%) | 1.5 | 6.9 | 4.9 | 10.7 |

As can be seen from the results summarized in the above table, the use of the oxide initiators in accordance with the process of this invention results in increased methane conversion and an increase in the hydrocarbon liquids formed.

While the invention has been explained in relation to its preferred embodiments, it is to be understood that the various modifications thereof will become apparent to those skilled in the art upon reading this specification. Therefore, it is to be understood that the invention disclosed herein is intended to cover such modifications as fall within the scope of the appended claims.

We claim:

1. A process for converting a feedstock comprising at least one light hydrocarbon to higher molecular weight hydrocarbon products and/or unsaturated hydrocarbon products comprising heating in the absence of solid catalyst a gaseous mixture comprising said feedstock and an added effective amount of at least one oxide initiator selected from the group consisting of nitrogen oxides, sulfur trioxide, and mixtures of these at a temperature of at least about 600° C. for a period of time effective to provide said conversion.

2. The process of claim 1 wherein the feedstock comprises methane, ethane and/or natural gas.

3. The process of claim 1 wherein the unsaturated hydrocarbon products comprise ethylene, acetylene, or mixtures thereof.

4. The process of claim 1 wherein the higher molecular weight products are liquid hydrocarbon products.

5. The process of claim 1 wherein the oxide is a nitrogen oxide including $N_2O$, $NO$, $N_2O_3$, $N_2O_4$, $N_2O_5$ or mixtures thereof.

6. The process of claim 1 wherein the oxide initiator is $N_2O$.

7. The process of claim 1 wherein the gaseous mixture contains from about 0.1 to about 30% by volume of the oxide initiator based on the volume of feedstock.

8. The process of claim 1 wherein the gaseous mixture is prepared and thereafter heated to a temperature above about 600° C.

9. The process of claim 1 wherein the gaseous mixture is heated to a temperature in the range of from about 850° C. to about 1500° C.

10. A process for converting a feedstock comprising at least one light hydrocarbon to higher molecular weight liquid hydrocarbon products comprising heating in the absence of solid catalyst a gaseous mixture comprising said feedstock and an added effective amount of at least one oxide initiator selected from the group consisting of nitrogen oxides, sulfur trioxide, and mixtures of these at a temperature of at least about 600° C. for a period of time effective to provide said higher molecular weight liquid hydrocarbon product.

11. The process of claim 10 wherein the gaseous mixture contains from about 0.1 to about 30% by volume of the oxide initiator based on the volume of feedstock.

12. The process of claim 10 wherein the gaseous mixture contains from about 0.1 to about 10% by volume of the oxide initiator based on the volume of feedstock.

13. The process of claim 10 wherein the light hydrocarbon is methane ethane and/or natural gas.

14. The process of claim 10 wherein the oxide initiator is a nitrogen oxide including $N_2O$, $NO$, $N_2O_3$, $N_2O_4$, $N_2O_5$ or mixtures thereof.

15. The process of claim 10 wherein the nitrogen oxide is $N_2O$.

16. The process of claim 10 wherein the gaseous mixture is prepared and thereafter heated to a temperature of at least about 600° C.

17. The process of claim 10 wherein the gaseous mixture is heated to a temperature within the range of about 850° to about 1500° C.

18. The process of claim 10 wherein the gaseous mixture is heated to a temperature within the range of about 1000° to about 1250° C.

19. The process of claim 10 wherein the gaseous mixture is heated for a period of from about 0.1 to about 3000 milliseconds.

20. The process of claim 10 wherein the gaseous mixture is heated for a period of from about 50 to about 500 milliseconds.

21. The process of claim 10 wherein the liquid product is recovered from the gases in the product, and the gases are recycled in the process.

22. The process of claim 10 conducted at a pressure of from 1 to about 10 atmospheres.

23. A process for converting a feedstock comprising methane, ethane, and/or natural gas to a liquid hydrocarbon product comprising heating in the absence of solid catalyst a gaseous mixture comprising said feedback and from about 0.1 to about 30% by volume of $N_2O$, $NO_2$ and/or $SO_3$ as initiator, based on the volume of feedstock, at a temperature within the range of from about 850° to about 1500° C. for a period of time sufficient to provide said liquid hydrocarbon product.

24. The process of claim 23 wherein the feedstock is natural gas.

25. The process of claim 23 wherein the feedstock is methane.

26. The process of claim 23 wherein the feedstock is ethane.

27. The process of claim 23 wherein the initiator is $N_2O$.

28. The process of claim 23 wherein the gaseous mixture comprises from about 0.1 to about 10% by volume of the initiator based on the volume of feedstock.

29. The process of claim 23 wherein the gaseous mixture is heated at a temperature of from about 1000° to about 1250° C.

30. The process of claim 23 wherein the gaseous mixture is heated for a period of from about 5 to about 800 milliseconds.

31. The process of claim 23 wherein the liquid hydrocarbon product is recovered from the gases, and the gases are recycled through the process.

32. A process for converting a feedstock comprising methane and/or natural gas to a liquid hydrocarbon product comprising heating in the absence of solid catalyst a gaseous mixture comprising said feedstock and from about 1 to about 10% by volume of $N_2O$ as initiator, based on the volume of feedstock, at a temperature of from about 1000 to about 1250° C. for a period of from about 1 to about 1000 milliseconds at a pressure of from about 1 to about 10 atmospheres.

* * * * *